United States Patent
Gerred et al.

(10) Patent No.: US 10,953,171 B2
(45) Date of Patent: Mar. 23, 2021

(54) DELIVERING VARIABLE POSITIVE AIRWAY PRESSURE DEPENDING ON AWAKE STATE AND SLEEP DISORDERED BREATHING

(71) Applicant: Fisher & Paykel Healthcare Limited, Auckland (NZ)

(72) Inventors: Andrew Gordon Gerred, Auckland (NZ); David Robin Whiting, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 719 days.

(21) Appl. No.: 15/301,332

(22) PCT Filed: Mar. 27, 2015

(86) PCT No.: PCT/IB2015/052255
§ 371 (c)(1),
(2) Date: Sep. 30, 2016

(87) PCT Pub. No.: WO2015/150997
PCT Pub. Date: Oct. 8, 2015

(65) Prior Publication Data
US 2017/0014585 A1    Jan. 19, 2017

Related U.S. Application Data

(60) Provisional application No. 61/974,310, filed on Apr. 2, 2014.

(51) Int. Cl.
*A61M 16/10*    (2006.01)
*A61M 16/00*    (2006.01)
(Continued)

(52) U.S. Cl.
CPC ....... *A61M 16/0003* (2014.02); *A61B 5/4806* (2013.01); *A61M 16/0069* (2014.02);
(Continued)

(58) Field of Classification Search
CPC ..... A61B 5/087; A61B 5/4806; A61B 5/4833; A61B 5/4836; A61M 16/0003;
(Continued)

(56) References Cited

U.S. PATENT DOCUMENTS 5,551,419 A * 9/1996 Froehlich ............ A61M 16/024
128/204.23
6,349,724 B1 * 2/2002 Burton ............... A61M 16/0057
128/204.18
(Continued)

FOREIGN PATENT DOCUMENTS

CN    103298512 A    9/2013
WO    WO 2008/039979 A2    4/2008
(Continued)

OTHER PUBLICATIONS

International Search Report; PCT/IB2015/052255; dated Jul. 22, 2015; 4 pages.
(Continued)

*Primary Examiner* — Annette Dixon
(74) *Attorney, Agent, or Firm* — Knobbe, Martens, Olson & Bear, LLP

(57) ABSTRACT

Positive airway pressure ("PAP") systems and methods are provided which supply a patient with a range of pressures for treatment when the patient is determined to be asleep, and an awake pressure for use when the patient is determined to be awake, the awake pressure configured for the comfort of the patient. The awake pressure is configured to be lower than the lower bound of the pressure range and can be a therapeutic or sub-therapeutic pressure. The PAP systems and
(Continued)

methods disclosed herein advantageously allow for the pressure range to be tailored for effective treatment of sleep disordered breathing while allowing the awake pressure to be set for the comfort of the patient. This can advantageously increase both the efficacy of the treatment of SDB and patient compliance with the treatment.

20 Claims, 4 Drawing Sheets

(51) Int. Cl.
*A61B 5/00* (2006.01)
*A61M 16/16* (2006.01)
*A61M 16/06* (2006.01)

(52) U.S. Cl.
CPC .......... *A61M 16/024* (2017.08); *A61M 16/06* (2013.01); *A61M 16/109* (2014.02); *A61M 16/16* (2013.01); *A61M 2016/0027* (2013.01); *A61M 2016/0033* (2013.01); *A61M 2016/0039* (2013.01); *A61M 2205/332* (2013.01); *A61M 2205/3375* (2013.01); *A61M 2205/3584* (2013.01); *A61M 2205/502* (2013.01); *A61M 2230/63* (2013.01)

(58) Field of Classification Search
CPC .......... A61M 16/0051; A61M 16/0057; A61M 16/0066; A61M 16/0069; A61M 16/024; A61M 16/06; A61M 16/107; A61M 16/109; A61M 16/16; A61M 16/202; A61M 16/204; A61M 16/205; A61M 2016/0021; A61M 2016/0027; A61M 2016/0033; A61M 2016/0036; A61M 2016/0039; A61M 2205/15; A61M 2205/332; A61M 2205/3334; A61M 2205/3344; A61M 2205/3355; A61M 2205/3365; A61M 2205/3375; A61M 2205/3584; A61M 2205/3653; A61M 2205/50; A61M 2205/502; A61M 2205/52; A61M 2230/10; A61M 2230/18; A61M 2230/60; A61M 2230/63; F04D 25/166; F04D 29/052; G06F 19/3481; G16H 40/63

See application file for complete search history.

(56) References Cited

U.S. PATENT DOCUMENTS

| | | | |
|---|---|---|---|
| 6,988,994 B2 | 1/2006 | Rapoport et al. | |
| 7,822,834 B2 | 10/2010 | Kawai et al. | |
| 8,528,551 B2* | 9/2013 | Mulcahy | A61M 16/0816 |
| | | | 128/204.21 |
| 9,440,037 B2* | 9/2016 | Mulcahy | A61M 16/0066 |
| 10,258,754 B2* | 4/2019 | Nightingale | A61M 16/0066 |
| 10,463,820 B2* | 11/2019 | Mulcahy | A61M 16/024 |
| 2008/0092894 A1 | 4/2008 | Nicolazzi et al. | |
| 2011/0166470 A1 | 7/2011 | Rapoport et al. | |
| 2013/0066226 A1 | 3/2013 | Welzien et al. | |

FOREIGN PATENT DOCUMENTS

| | | |
|---|---|---|
| WO | WO 2011/006199 A1 | 1/2011 |
| WO | WO 2012/020314 A2 | 2/2012 |
| WO | WO 2012/075433 A2 | 6/2012 |
| WO | WO 2013/172722 A1 | 11/2013 |
| WO | WO 2014/007659 A1 | 1/2014 |

OTHER PUBLICATIONS

Office Action from corresponding Chinese Patent Application No. 201580024432.9, dated Jun. 5, 2018, in 16 pages.
Search Report in corresponding French Patent Application No. 1552566, dated Mar. 26, 2015, in.
Examination Report in corresponding European Patent Application No. 15773138.1, dated Oct. 13, 2017, in 7 pages.
Examination Report in corresponding European Patent Application No. 15773138.1, dated Sep. 5, 2018, in 3 pages.
Office Action in corresponding Australian Patent Application No. 2015242215, dated Jun. 4, 2019, in 5 pages.
Office Action in corresponding Japanese Patent Application No. 2016-560407, dated Nov. 1, 2019, in 3 pages.
Examination Report in corresponding Australian Patent Application No. 2015242215, dated May 29, 2020, in 3 pages.

* cited by examiner

DELIVERING VARIABLE POSITIVE AIRWAY PRESSURE DEPENDING ON AWAKE STATE AND SLEEP DISORDERED BREATHING

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present disclosure relates to systems for treating obstructive sleep apnea by providing positive airway pressure to a patient, in particular, to methods for the device to adjust the treatment pressure in response to the patient's awake state and sleep disordered breathing.

Description of Related Art

One major treatment approach for obstructive sleep apnea includes providing breathing gases to the patient throughout the period the patient is asleep. These treatments may collectively be known as positive airway pressure therapy (PAP). Variations on this therapy include having different inspiration and expiration pressures, commonly known as bi-level or bi-PAP, or having continuously adjusting therapy which responds to breathing events.

SUMMARY

The systems, methods and devices described herein have innovative aspects, no single one of which is indispensable or solely responsible for their desirable attributes. Without limiting the scope of the claims, some of the advantageous features will now be summarized.

The present disclosure describes a positive airway pressure system that delivers gas to a patient when asleep, the gas having a pressure within a range of asleep pressures, and a different awake pressure when the patient is awake, the awake pressure being lower than the minimum pressure in the range of asleep pressures. This can advantageously improve the comfort of the device for a patient, which can increase compliance with the positive airway pressure therapy. Increased compliance generally improves the results of the therapy for the patient.

In a first aspect, a positive airway pressure system is provided which includes a flow generator configured to provide gas at a pressure to a patient. The positive airway pressure system also includes a user interface configured to provide to the patient the gas at the pressure and a conduit that provides a path for the gas from the flow generator to the user interface. The positive airway pressure system also includes a sensor configured to measure breathing of the patient. The positive airway pressure system also includes a control system configured to detect sleep disordered breathing based at least in part on analysis of data acquired by the sensor; determine a sleep state of the patient based at least in part on analysis of data acquired by the sensor; control the flow generator to provide a pressure between a low pressure and a high pressure when the sleep state is determined to be asleep, the pressure provided based at least in part on whether sleep disordered breathing is detected; and control the flow generator to provide an awake pressure different from the low pressure if the sleep state is determined to be awake, the awake pressure is selected by a user.

In some embodiments of the first aspect, the awake pressure is a therapeutic pressure. In some embodiments of the first aspect, the awake pressure is lower than the low pressure.

In some embodiments of the first aspect, the controller is further configured to control the flow generator to provide a pressure which increases over time at a first pressure ramp rate when the pressure being provided by the flow generator is the awake pressure and the sleep state is determined to be asleep or sleep disordered breathing is detected. In a further embodiment, the first pressure ramp rate is adjustable by a user. In some embodiments of the first aspect, the controller is further configured to control the flow generator to provide a pressure which decreases over time at a second pressure ramp rate when the pressure being provided by the flow generator is between the low pressure and the high pressure and the sleep state is determined to be awake. In a further embodiment, the second pressure ramp rate is adjustable by a user.

In some embodiments of the first aspect, the low pressure and the high pressure are adjustable by a user. In some embodiments of the first aspect, the sensor is one of a flow sensor, a pressure sensor, a sound sensor, a motion sensor, or a plethysmograph sensor.

In a second aspect, a method is provided for supplying positive airway pressure therapy to a patient. The method includes receiving input from a user to set an awake pressure, detecting a presence of sleep disordered breathing; determining a sleep state of the patient; if the sleep state is determined to be asleep, delivering gas having an asleep pressure that is adjusted between a low asleep pressure and a high asleep pressure, the asleep pressure depending at least in part on the presence of sleep disordered breathing; and if the sleep state is determined to be awake, delivering gas having the awake pressure, the awake pressure different from the low asleep pressure.

In some embodiments of the second aspect, the awake pressure is a therapeutic pressure. In some embodiments of the second aspect, the awake pressure is lower than the low asleep pressure.

In some embodiments of the second aspect, the method further includes increasing a pressure of the gas delivered at a first ramp rate when the pressure being delivered has the awake pressure and the sleep state is determined to be asleep or sleep disordered breathing is detected. In a further aspect, the method includes receiving input from a user to set the first ramp rate.

In some embodiments of the second aspect, the method includes decreasing a pressure of the gas delivered at a second ramp rate when the pressure being delivered is between the low asleep pressure and the high asleep pressure and the sleep state is determined to be awake. In a further aspect, the method includes receiving input from a user to set the second ramp rate.

In some embodiments of the second aspect, the method includes receiving input from a user to set the low asleep pressure and the high asleep pressure. In some embodiments of the second aspect, detecting a presence of sleep disordered breathing comprises analyzing values from a sensor, the sensor comprising at least one of a flow sensor, a pressure sensor, a sound sensor, a motion sensor, or a plethysmograph.

In a third aspect, a user interface is provided that is communicably coupled to a control system of a positive airway pressure apparatus. The user interface includes an awake pressure node configured to receive awake pressure data indicative of an awake pressure. The user interface includes a low pressure node configured to receive lower bound data indicative of a lower bound of a pressure range. The user interface includes a high pressure node configured to receive upper bound data indicative of an upper bound of the pressure range. The user interface communicates the awake pressure, the lower bound of the pressure range, and the upper bound of the pressure range to the control system, and the control system controls the positive airway pressure apparatus to supply a breathing gas having the awake pressure if a sleep state is determined to be awake, the awake pressure is different from the lower bound of the pressure range.

In some embodiments of the third aspect, the awake pressure is less than the lower bound of the pressure range. In some embodiments of the third aspect, the user interface further includes a ramp rate node configured to receive ramp rate data indicative of a pressure ramp rate. In a further embodiment of the third aspect, the control system transitions from providing the awake pressure to a pressure within the pressure range at the pressure ramp rate.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

DETAILED DESCRIPTION

Figure 1:
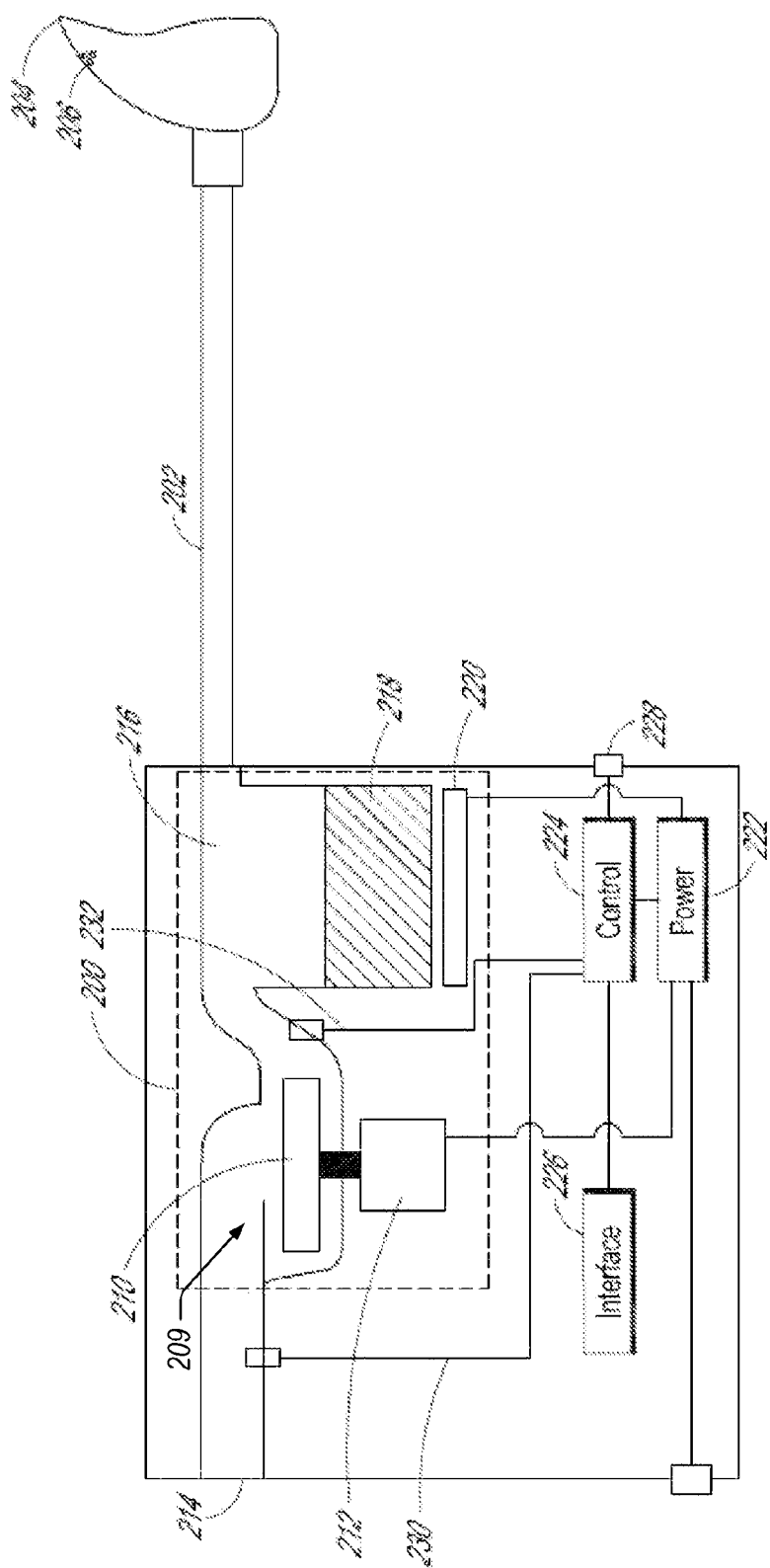
FIG. 1 illustrates a PAP system configured to provide PAP therapy to a patient, wherein the PAP system includes a flow generator, a controller, a patient interface, and a conduit connecting the patient interface and the flow generator.

Certain embodiments and examples of systems and methods for providing positive airway pressure are described herein. The systems and methods generally include providing a range of pressures to treat sleep disordered breathing when a patient is determined to be asleep and an awake pressure when the patient is determined to be awake. The range of pressures and the awake pressure can include therapeutic and/or sub-therapeutic pressures. Those of skill in the art will appreciate that the disclosure extends beyond the specifically disclosed embodiments and/or uses and obvious modifications and equivalents thereof. Thus, it is intended that the scope of the disclosure not be limited by any particular embodiments described herein.

As used herein, the term sleep disordered breathing is a broad term and is intended to have its plain and ordinary meaning to those of ordinary skill in the art and includes at least any of a group of disorders characterized by abnormalities of respiratory pattern (e.g., pauses in breathing). Sleep disordered breathing includes, for example and without limitation, obstructive sleep apnea, upper-airway resistance syndrome, Cheyne-Stokes respiration, and the like.

As used herein, the term therapeutic pressure is a broad term and is intended to have its plain and ordinary meaning to those of ordinary skill in the art and includes at least a pressure configured to be effective in treating sleep disordered breathing. A sub-therapeutic pressure, by comparison, is a pressure that is below the pressure which is effective for treating sleep disordered breathing. Whether a pressure is therapeutic can be patient- and/or time-dependent. For example, a pressure of 10 cmH2O can be a therapeutic pressure at one instance in time for a particular patient because it would reduce or eliminate in that patient sleep disordered breathing at that time and, by extension, any pressure below 10 cmH2O would be a sub-therapeutic pressure for that patient at that time.

Positive airway pressure ("PAP") systems can be configured to provide a continuously adjustable pressure configured to treat sleep disordered breathing ("SDB"). A pressure algorithm can be used which analyzes a patient's breathing to determine a pressure to deliver to the patient. The pressures to be delivered to the patient, or the pressures determined by the pressure algorithm for delivery to the patient, can be constrained to be within a pressure range. The pressures within the pressure range, however, can be uncomfortable for a patient who is awake or who awakens during treatment. In some PAP systems, then, the minimum pressure of the pressure range can be delivered when the patient is determined to be awake to reduce discomfort to the patient.

There are competing interests in this situation which may reduce or prevent effective treatment of SDB. First, it is desirable to set the pressure range for effective treatment of SDB. It is desirable, for example, to restrict the amount of pressure adjustability (e.g., by restricting the size of the pressure range). Restricting the amount of pressure variability may reduce the likelihood of SDB events due at least in part to inappropriately applied sub-therapeutic pressures. Restricting the amount of pressure variability may also reduce or prevent transient large swings in pressure and reduce or prevent inappropriate or undesirable pressure increases.

Second, it is desirable to set the lower bound of the pressure range for the comfort of the patient when awake. Generally, the lower the pressure the more comfortable the treatment is for a patient while they are awake. Accordingly, it may be desirable to set the lower bound of the treatment range to a relatively low pressure setting or the lowest available pressure setting (e.g., about 4 cmH2O). However, a comfortable pressure may not effectively treat SDB. Setting the lower bound of the pressure range to be comfortable for the patient, then, makes it so that the pressure algorithm is less effective in treating SDB. Thus, if the lower bound of the pressure range is configured to be comfortable for the patient while awake, there may be confusion or a conflict on the part of the clinician, physician, or user on how to set this pressure. For example, there may be a conflict or confusion regarding whether the lower bound should be set for comfort while the patient is awake or whether it should be set higher to provide effective therapy while asleep.

Accordingly, PAP systems and methods are provided which utilize an additional parameter, the awake pressure, to address these issues. The PAP systems and methods disclosed herein provide for a pressure treatment range for use when the patient is determined to be asleep, and an awake pressure for use when the patient is determined to be awake, the awake pressure configured for the comfort of the patient. The awake pressure is configured to be lower than or equal to the lower bound of the pressure range and can be a therapeutic or sub-therapeutic pressure. The awake pressure can differ depending at least in part on the preference of the patient. The PAP systems and methods disclosed herein advantageously allow for a physician, clinician, or user to tailor the pressure range for effective treatment of SDB while allowing the awake pressure to be set for the comfort of the patient. This can advantageously increase both the efficacy of the treatment of SDB and patient compliance with the treatment.

Positive Airway Pressure Apparatus

FIG. 1 is a diagram illustrating an example PAP system configured to supply breathing gases with pressures determined as described herein. The system includes an apparatus 200 for delivering a supply of breathing gases, a supply conduit 202, and a patient interface 204. The pressure of the breathing gases provided by the apparatus 200 can vary based on conditions detected by the system. The system can vary the provided pressure in response to sleep disordered breathing, where the variation in the pressure can be constrained to be within lower and upper bounds. The system can provide an awake pressure when a patient is determined to be awake, the awake pressure lower than or equal to the lower bound of the pressure range.

The system includes the supply conduit 202 which extends from an outlet of the gases supply apparatus to the patient interface 204. The supply conduit 202 is configured to deliver the pressurized breathing gases to the patient interface 204. The patient interface 204 includes a bias flow vent 206 for allowing a controlled leak from the patient interface 204. The controlled leak allows the inside of the patient interface 204 to be continuously flushed by fresh gases supplied by the supply apparatus 200. The patient interface 204 may comprise any of the many types of typical patient interface for PAP delivery, for example, nasal mask, full face mask, oral mask, oral interface, nasal pillows, nasal seal or nasal cannula. The bias flow vent 206 may be located directly on the patient interface 204, or adjacent the patient interface 204 on a connector between the patient interface 204 and the supply conduit 202 or through the wall of the supply conduit 202, close to the patient interface 204. A wide variety of patient interfaces and conduits are known in the art.

The apparatus 200 includes a flow generator 209. The flow generator 209 can comprise a fan 210 driven by an electric motor 212. Air is drawn through an inlet 214 in the housing of the apparatus 200 by the fan 210. Pressurized air leaves the fan 210 for delivery to the patient through supply conduit 202 and patient interface 204. In some embodiments, controllable flow generators may draw on a source of high pressure gas, and regulate a flow of gas from the high pressure source.

The apparatus 200 may include a humidifier 216, for example in the form of a pass-over humidifier where air passing through the humidifier chamber picks up a quantity of water vapor from a water reservoir 218. The water reservoir 218 may be heated by a heater 220. The humidifier 216 may be integrated with the housing of the flow generator 209 or a separate, optional, component.

The heater 220 and motor 212 are supplied with power from a power supply 222. The amount of power to the motor 212 and the amount of power to the heater 220 can be controlled by the control system 224. The control system 224 is also supplied with power from the power supply 222.

The control system 224 can be configured to receive input from a user interface 226. For example, the control system 224 can receive user input to set the pressure range and/or the awake pressure, as well as other parameters associated with the operation of the apparatus 200.

The control system 224 may also include a communication port 228 for connecting with an external data source or other external system. The external data source or system may, for example, include a communication interface such as a modem or router, or may be an interface to an external memory such as a smart card, disk drive, flash memory or the like. For generic use, the communication port 228 may be a data communication port according to any of the many available standards, for example, a universal serial bus (USB) port. A USB (or similar) interface can be used for connecting a wide range of peripheral devices.

As described in greater detail with reference to FIG. 2, the control system 224 can include a controller such as a computer processor (e.g., an embedded microcomputer with stored control programs). In certain embodiments, the control system 224 may comprise a fixed electronic circuit implementing programmed functionality, or a programmed logic circuit (such as an FPGA) implementing the programmed functionality. In addition, the control system 224 can include a non-transitory storage medium such as computer memory configured to store executable instructions that, when executed, cause the controller to perform programmed functions. Examples of programmed functions include determination of a pressure setpoint, determination of a patient sleep state, detection of sleep disordered breathing, or other functions to control the apparatus 200.

The apparatus 200 can include one or more sensors. The one or more sensors can include a flow sensor 230 and may also include a pressure sensor 232 downstream of the fan 210. The flow sensor 230 may be upstream or downstream of the fan 210. The one or more sensors can include, for example and without limitation, the flow sensor 230, the pressure sensor 232, a sound sensor, a motion sensor, a plethysmograph, and the like.

The control system 224 can be configured to receive data acquired by the one or more sensors. Based at least in part on the acquired data, the control system 224 can be configured to detect a sleep state of the patient. Similarly, based at least in part on the acquired data, the control system 224 can be configured to detect sleep disordered breathing. When the patient is asleep, the control system 224 can utilize a pressure algorithm to determine an appropriate or targeted pressure of breathing gases to supply to the patient wherein the pressure determined by the pressure algorithm is based at least in part on any detected sleep disordered breathing events. When the patient is determined to be awake, the control system 224 can be configured to control the apparatus 200 to deliver the awake pressure.

The pressure algorithm can be configured to determine a target pressure for supplied breathing gases, the target pressure based at least in part on current and/or historical supplied pressure and the presence of sleep disordered breathing. In some embodiments, the pressure algorithm can increase the pressure of the supplied breathing gases when sleep disordered breathing is detected. In some instances, the pressure can continue to increase (e.g., in discrete or continuous pressure increments) while the sleep disordered breathing continues. In some instances, the pressure can decrease (e.g., in discrete or continuous pressure decrements) while there is no sleep disordered breathing.

The pressure algorithm can be limited to a range of pressures. For example, the control system 224 can provide a minimum pressure and a maximum pressure to the pressure algorithm such that the pressure algorithm is restricted to output pressures within the range inclusive of the minimum and maximum pressures. The range of pressures can include therapeutic pressures, sub-therapeutic pressures, or both therapeutic and sub-therapeutic pressures. The range of pressures can be configured such that the minimum and maximum pressures bracket a determined, targeted, or optimal pressure. For example, where it is determined that a pressure of approximately 12 cmH2O is an effective therapeutic pressure for a patient, the lower bound of the pressure range can be set to 9 cmH2O and the upper bound of the pressure range can be set to 15 cmH2O. By setting this range, the control system 224 allows the pressure algorithm to respond to changes in patient state that merit or require different pressures but limits or prevents the apparatus 200 from providing under- and/or over-treatment. For example, where the pressure algorithm determines that an appropriate or optimal pressure for a patient is approximately 12 cmH2O, this value may change depending on whether the patient is sleeping on their back or on their side. Other factors may affect an appropriate or therapeutic pressure including, for example and without limitation, alcohol consumption, sleep states, a patient's physical characteristics, and the like.

When the patient is awake, the control system 224 can be configured to control the apparatus 200 to supply breathing gases at an awake pressure that is lower than or equal to the lower bound of the pressure range utilized by the pressure algorithm. The awake pressure can be configured to be more comfortable for the patient relative to the pressures in the pressure range. Increasing the comfort of the patient can increase compliance with the positive airway pressure therapy, thereby increasing the efficacy of the treatment. The awake pressure can be a therapeutic or a sub-therapeutic pressure. The awake pressure can be adjusted and/or selected by a patient, physician, user, clinician, or the like.

The control system 224 can be configured to control the apparatus 200 to transition between supplying breathing gases at the awake pressure and supplying breathing gases within the pressure range. When a change in a patient's sleep state is determined by the control system 224, the control system 224 can employ a transition function to ramp the pressure up or down between the awake pressure and the pressure range, depending on whether the patient is waking up or falling asleep.

Positive Airway Pressure Control System

Figure 2:
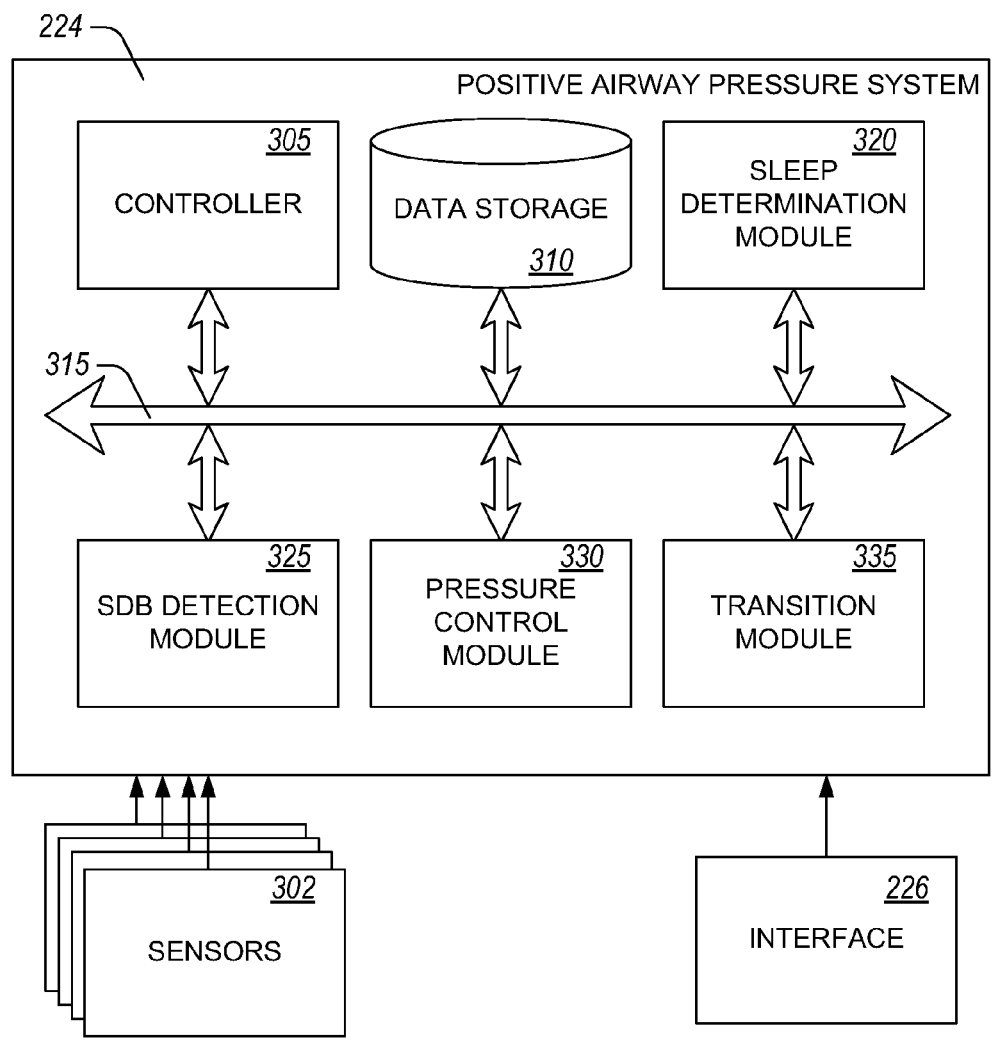
FIG. 2 illustrates a block diagram of an example PAP system configured to provide an awake pressure when a patient is awake and a range of pressures when the patient is asleep, the minimum pressure in the range being different than the awake pressure.

FIG. 2 illustrates a block diagram of an example PAP control system 224 configured to control a PAP apparatus (e.g., the apparatus 200 described with reference to FIG. 1) to provide an awake pressure when a patient is awake and a range of pressures when the patient is asleep, the lower bound of the pressure range being greater than the awake pressure. The control system 224 can be configured to receive input from sensors 302 and/or patient interface 204, to determine a sleep state of a patient, to detect sleep disordered breathing, to determine a targeted pressure based at least in part on input received from the sensors and/or user, and/or to control a flow generator to supply breathing gases having the targeted pressure. The sensors 302 can include one or more of a flow sensor, a pressure sensor, a sound sensor, a motion sensor, and/or a plethysmograph. The interface 226 can be any suitable system which allows a user to provide data to the control system, such as through a touch screen interface, a keyboard, a display, buttons, switches, or any combination of these or similar elements. The control system 224 can be implemented using hardware, software, firmware, or any combination of these.

The control system 224 includes a controller 305 comprising one or more computer processors. The control system 224 includes data storage 310 comprising non-transitory computer memory. The control system 224 includes modules 320, 325, 330, 335 configured to analyze sensor data and user input to determine a targeted pressure to supply to a patient. In some embodiments, one or more of the modules 320, 325, 330, or 335 utilizes the controller 305 and/or data storage 310 to accomplish its functionality. The controller 305, data storage 310, and modules 320, 325, 330, and 335 can be configured to communicate with one another over communications bus 315. The communications bus 315 can be any standard communications bus. The communications bus 315 can at least partially include a networked connection, using either wireless or wired connections. The communication bus 315 can include communication between processes or functions being executed by one or more of the modules 320, 325, 330, or 335 and/or the controller 305.

The control system 224 includes the sleep determination module 320 configured to analyze data acquired by one or more of the sensors 302 to determine a sleep state of a patient. In some embodiments, the sleep determination module 320 assigns the sleep state of the patient to be either asleep or awake. Generally, the sleep determination module 320 can analyze sensor data to identify breathing patterns indicative of sleep. Any suitable methods of making a determination that the user is asleep or is awake can be used. Some suitable methods are described in other patent publications, for example, U.S. Pat. No. 6,988,994 and U.S. Pat. Pub. No. 2008/0092894, each of which is hereby incorporated by reference in its entirety.

The control system 224 includes the SDB detection module 325 configured to analyze data acquired by one or more of the sensors 302 to detect SDB events such as apneas, hypopneas, flow limitations, or the like. Generally, the SDB detection module 325 can analyze sensor data to identify breathing patterns indicative of SDB events. Examples of techniques used to detect SDB events are disclosed in U.S. Pat. No. 7,882,834 to Gardon et al., entitled "Autotitrating Method and Apparatus," issued Feb. 8, 2011, the entire contents of which is hereby incorporated by reference in its entirety.

The control system 224 includes the pressure control module 330 configured to analyze the sleep state of the patient and any SDB events to determine a pressure of a breathing gas to supply to the patient. For example, if the patient is awake, the pressure control module 330 can indicate to the control system 224 that the awake pressure should be supplied to the patient. If, on the other hand, the patient is asleep, the pressure control module 330 can utilize a control algorithm to determine the pressure to supply to the patient, the pressure being within the pressure range (e.g., not to exceed the upper bound of the pressure range or the maximum pressure and not to be below the lower bound of the pressure range or the minimum pressure). The pressure control module 330 can take into account the presence of one or more SDB events and adjust the targeted pressure output in response. Various methods of control or control algorithms are possible, including the methods described in PCT Publication Number WO 2012/020314, filed Aug. 12, 2011 and entitled "APPARATUS AND METHOD FOR PROVIDING GASES TO A USER," which is incorporated by reference herein in its entirety. Other examples of control methods include, for example, multi-night, auto-cpap, bi-level, auto bi-level, and the like.

The control system 224 includes the transition module 335 configured to monitor transitions between the awake and asleep sleep states. The transition module 335 can work in conjunction with the pressure control module 330 to transition between the awake and asleep control modes. For example, when transitioning from an awake state to a sleep state, the transition module 335 can ramp up the pressure from the awake pressure to the lower bound of the pressure range. Once the pressure reaches the pressure range, the pressure control module 330 can take over control of determining the pressure to supply to the patient. As another example, the transition from the sleep state to the awake state can similarly be handled by the transition module 335 which can ramp down the pressure from the pressure range to the awake pressure. The ramp rates for increasing the pressure and decreasing the pressure can be the same or different from one another. The ramp rates may also be selected or adjusted by a user of the system, such as a clinician, a patient, or a physician. In some embodiments, the transition module 335 is configured to ignore SDB events during the transition from the awake state to the sleep state. In some embodiments, if the patient awakes during the transition to the pressure range from the awake pressure, the transition module 335 can ramp the pressure down from the pressure at the time the transition occurred to the awake pressure.

Figure 3:
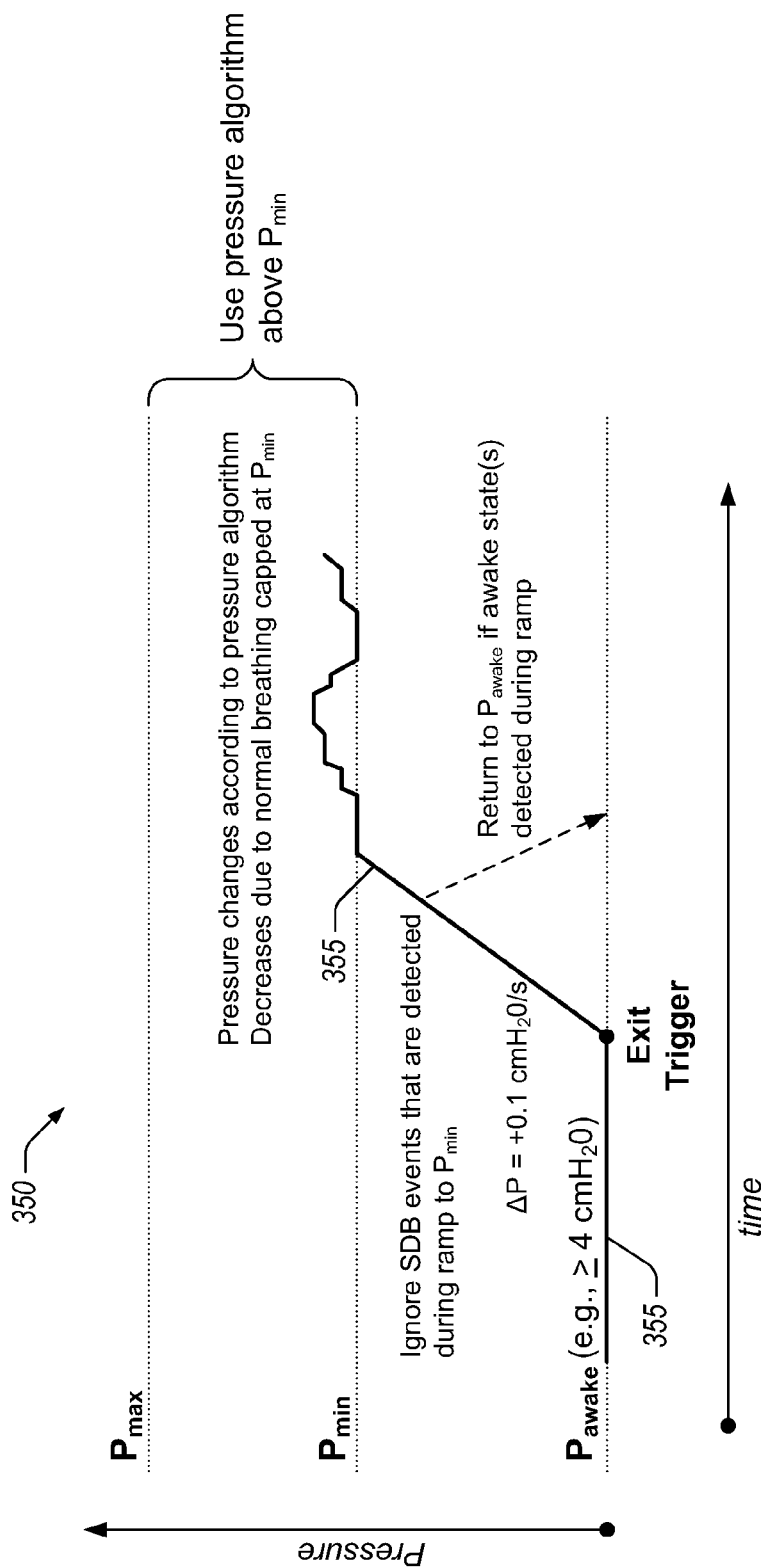
FIG. 3 illustrates a plot of pressure for delivery to a patient as a function of time, the plot demonstrating different events and responses to the events.

FIG. 3 illustrates a plot 350 of a pressure of breathing gases supplied to a patient as a function of time, the plot demonstrating different events and responses to the events. The line 355 represents the pressure supplied to a patient over time. Initially, the pressure supplied to the patient is the awake pressure, or Pawake. The awake pressure can have a relatively low value, such as greater than or equal to about 4 cmH2O or less than about 4 cmH2O.

While the patient is awake, the pressure supplied remains the awake pressure. Upon the occurrence of an exit trigger, the pressure ramps up to the pressure range, or a pressure between Pmin and Pmax, inclusive. The exit trigger can be, for example and without limitation, two apnea events (e.g., central or obstructive) within a moving window of 30 consecutive breaths, two hypopnea events (e.g., central or obstructive) within a moving window of 30 consecutive breaths, or an event with a sequence of three flow-limited breaths in a row. It is to be understood that the exit trigger can comprise more than just a transition from an awake sleep state to an asleep sleep state, but can also include other indications that the patient is asleep, such as apnea events, hypopnea events, and so forth.

Upon the occurrence of an exit trigger, the pressure supplied increases from the awake pressure to at least the lower bound of the pressure range. The rate of change of pressure can be configured to reduce or minimize discomfort to the patient. The rate of change can be configured or adjusted by a user, such as a clinician, patient, or physician. An example rate of change from the awake pressure to the pressure range is about +0.1 cmH2O/s. Other values can also be used, such as at least about +0.02 cmH2O/s and/or less than or equal to about +2 cmH2O/s, at least about +0.05 cmH2O/s and/or less than or equal to about +1 cmH2O/s, or at least about +0.1 cmH2O/s and/or less than or equal to about +0.5 cmH2O/s.

During the transition from the awake pressure to the pressure range, certain events can be ignored. For example, SDB events can be ignored during the transition as the events will be treated using the pressures within the pressure range. Increasing the pressure at a higher rate than the designated ramp rate may cause discomfort to the patient. In some embodiments, the ramp rate can change in response to one or more SDB events.

During the transition from the awake pressure to the pressure range, if the sleep state of the patient is determined to be awake. At this point, the supplied pressure can be reduced from its current value to the awake pressure. The rate of change to the awake pressure can have the same magnitude as the rate of change of increase from the awake pressure or it can be different. An example rate of change to the awake pressure is about −0.1 cmH2O/s. Other values can also be used, such as where the magnitude of the change is at least about 0.02 cmH2O/s and/or less than or equal to about 2 cmH2O/s, at least about 0.05 cmH2O/s and/or less than or equal to about 1 cmH2O/s, or at least about 0.1 cmH2O/s and/or less than or equal to about 0.5 cmH2O/s.

Once the pressure reaches the lower bound of the pressure range (e.g, Pmin), the pressure algorithm can be used to control the pressure, as described in greater detail herein. For example, the supplied pressure can be increased in response to an SDB event. Similarly, the pressure can decrease where the patient is breathing normally. In both instances, the range of pressures provided through the pressure algorithm is capped, having a lower bound at Pmin and an upper bound at Pmax. As an example, the pressure range can extend from about 4 cmH2O to about 20 cmH2O, where Pmin is greater than or equal to 4 cmH2O, Pmax is less than or equal to 20 cmH2O, Pmin is less than Pmax, and Pmin is greater than Pawake.

If the patient awakes while the pressure is within the pressure range, the pressure supplied can decrease at the designated rate of change to the awake pressure.

Method of Delivering Positive Airway Pressure

Figure 4:
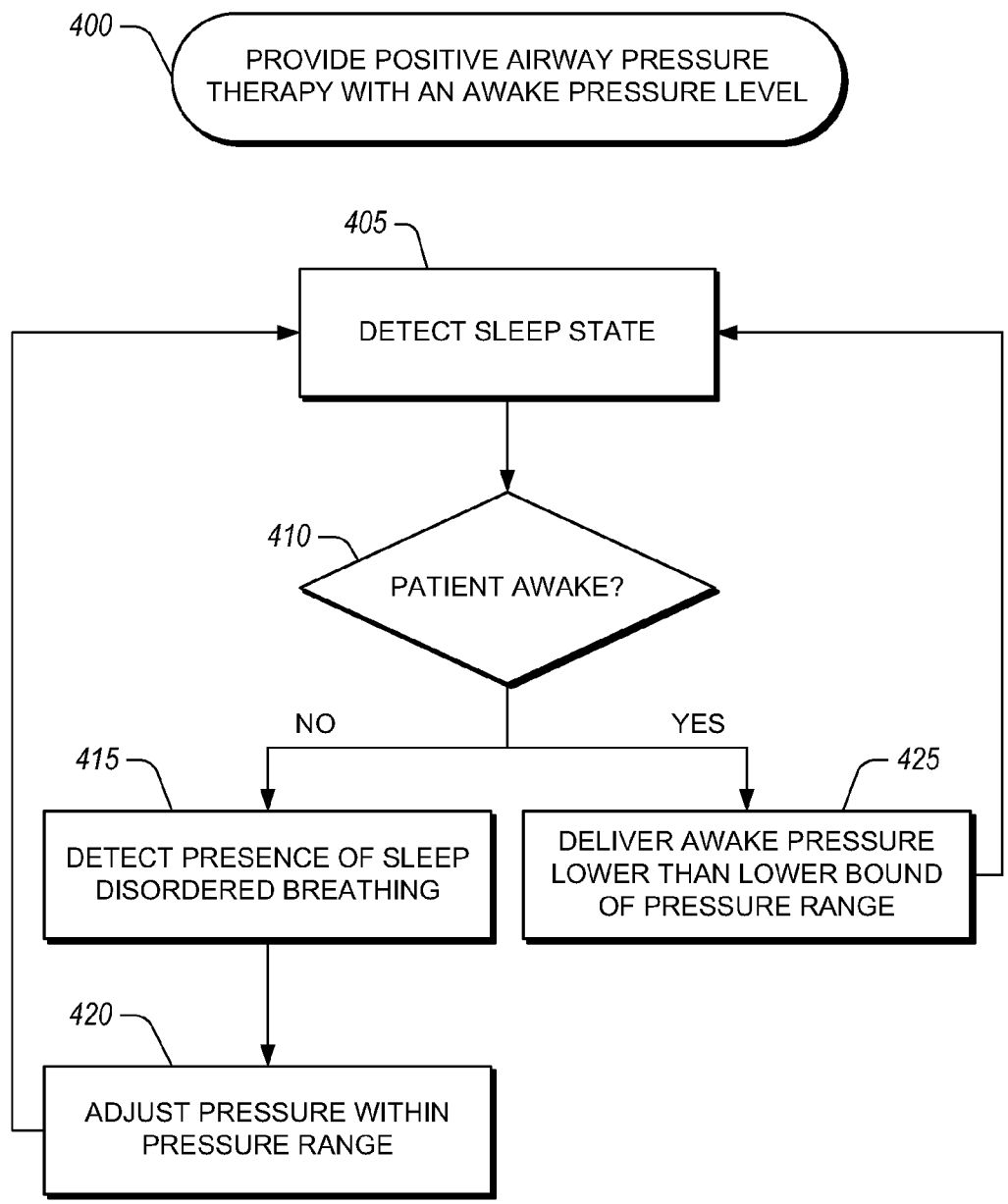
FIG. 4 illustrates a flow chart of an example method of delivering an awake pressure to a patient and a range of pressures when the patient is asleep, the minimum pressure in the range being different from the awake pressure.

FIG. 4 illustrates a flow chart of an example method 400 of delivering an awake pressure to a patient and a range of pressures when the patient is asleep, the minimum pressure in the range being different from the awake pressure. For ease of description, the steps of the method 400 will be described as being performed by the control system 224. However, one or more steps of the method can be performed by one or more components of the apparatus 200 and/or the modules 320, 325, 330, 335. In addition, a single step or a combination of steps can be accomplished through the combined efforts and functionality of the systems and modules described herein.

In block 405, the control system 224 detects a sleep state of the patient. By monitoring one or more sensors, the control system 224 can detect the sleep state and make a determination of whether the patient is asleep or awake. In some embodiments, the sleep state is detected through monitoring of breathing patterns. Any suitable method of determining the sleep state of the patient can be used. Some suitable methods are described in other patent publications, for example, U.S. Pat. No. 6,988,994 and U.S. Pat. Pub. No. 2008/0092894, each of which is hereby incorporated by reference in its entirety.

In block 410, the control system 224 proceeds along different control loops depending on whether the patient is awake. If the patient is asleep, the method 400 continues to block 415 where the control system detects sleep disordered breathing. The control system 224 can analyze sensor data to detect SDB events. Examples of techniques used to detect SDB events are disclosed in U.S. Pat. No. 7,882,834 to Gradon et al., entitled "Autotitrating Method and Apparatus," issued Feb. 8, 2011, the entire contents of which is hereby incorporated by reference in its entirety.

If the control system 224 is transitioning from an awake state to a sleep state, or if the pressure is transitioning to the pressure range (e.g., whether or not it starts at the awake pressure), the pressure can change with a rate of change configured to reduce or eliminate discomfort associated with large pressure changes. The rate of change of pressure, or the ramp up rate, can be selected, adjusted, or configured by a user. In some embodiments, the ramp up rate can be a constant or it can vary based at least in part on data acquired with the sensors or other relevant data. During the transition, the control system 224 can be configured to ignore SDBs detected in block 415.

When the pressure reaches the pressure range, the control system 224 can employ control methods which adjust the pressure within the pressure range based at least in part on any detected SDB events or lack thereof (e.g., normal breathing) in block 420. Various methods of control or control algorithms are possible, including the methods described in PCT Publication Number WO 2012/020314, filed Aug. 12, 2011 and entitled "APPARATUS AND METHOD FOR PROVIDING GASES TO A USER," which is incorporated by reference herein in its entirety.

If the patient is awake, the method 400 proceeds from block 410 to block 425 where the control system 224 controls the PAP system to supply breathing gases at an awake pressure, the awake pressure lower than or equal to the lower bound of the pressure range. If the control system 224 is transitioning from an asleep state to an awake state, or if the pressure is transitioning to the awake pressure (e.g., whether or not it starts in the pressure range), the pressure can change with a rate of change configured to reduce or eliminate discomfort associated with large pressure changes. The rate of change of pressure, or the ramp down rate, can be selected, adjusted, or configured by a user. In some embodiments, the ramp down rate can be a constant or it can vary based at least in part on data acquired with the sensors or other relevant data.

After completion of the operations in block 420 or block 425, the method 400 then returns to block 405 where the control system 224 detects the sleep state of the patient. The control loop can thus proceed in a continuous loop to control the PAP system and respond to changes in the patient's sleep state and to sleep disordered breathing events.

CONCLUSION

Examples of PAP systems and methods which provide a range of pressures for sleeping patients and a lower pressure for awake patients have been described with reference to the figures. The representations in the figures have been presented to clearly illustrate principles related to PAP therapy having an awake pressure setting, and details regarding divisions of modules or systems have been provided for ease of description rather than attempting to delineate separate physical embodiments. The examples and figures are intended to illustrate and not to limit the scope of the embodiments described herein.

As used herein, the term "controller" or "processor" refers broadly to any suitable device, logical block, module, circuit, or combination of elements for executing instructions. For example, the controller 305 can include any conventional general purpose single- or multi-chip microprocessor such as a Pentium® processor, a MIPS® processor, a Power PC® processor, AMID® processor, ARM® processor, or an ALPHA® processor. In addition, the controller 305 can include any conventional special purpose microprocessor such as a digital signal processor. The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. The controller 305 can be implemented as a combination of computing devices, e.g., a combination of a DSP and a microprocessor, a plurality of microprocessors, one or more microprocessors in conjunction with a DSP core, or any other such configuration.

Data storage 310 can refer to electronic circuitry that allows information, typically computer or digital data, to be stored and retrieved. Data storage 310 can refer to external devices or systems, for example, disk drives or solid state drives. Data storage 310 can also refer to fast semiconductor storage (chips), for example, Random Access Memory (RAM) or various forms of Read Only Memory (ROM), which are directly connected to the communication bus or the controller 305. Other types of memory include bubble memory and core memory. Data storage can be physical hardware configured to store information in a non-transitory medium.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments. As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is otherwise understood with the context as used in general to convey that an item, term, etc. may be either X, Y or Z. Thus, such conjunctive language is not generally intended to imply that certain embodiments require at least one of X, at least one of Y and at least one of Z each to be present. Language used herein connoting approximation, estimation, or inexact values, such as, among others, "around," "about," "approximately," and the like, unless specifically stated otherwise, or otherwise understood within the context as used, is generally intended to convey that the values described by the language are within 10% of the stated value, within 5% of the stated value, or within 1% of the stated value.

It should be emphasized that many variations and modifications may be made to the embodiments described herein, the elements of which are to be understood as being among other acceptable examples. All such modifications and variations are intended to be included herein within the scope of this disclosure and protected by the following claims. Further, nothing in the foregoing disclosure is intended to imply that any particular component, characteristic or process step is necessary or essential.

The invention claimed is:

1. A positive airway pressure device comprising:
a flow generator configured to provide gas at a pressure to a patient;
a sensor configured to measure breathing of the patient; and
a control system configured to:
detect sleep disordered breathing based at least in part on analysis of data acquired by the sensor;
determine a sleep state of the patient based at least in part on analysis of data acquired by the sensor;
control the flow generator to provide a pressure between a low pressure that is greater than or equal to about 4 cmH2O and a high pressure that is less than or equal to about 20 cmH2O in response to the control system determining the sleep state to be asleep during a treatment session, the pressure provided based at least in part on whether sleep disordered breathing is detected; and
control the flow generator to provide an awake pressure different from the low pressure in response to the control system determining the sleep state to be awake based on breathing patterns detected from the patient after a previously determined asleep state during the treatment session, the awake pressure being selected by a user and a therapeutic pressure greater than or equal to about 4 cmH2O.

2. The positive airway pressure device of claim 1, wherein the control system is further configured to control the flow generator to provide a pressure which increases over time at a first pressure ramp rate when the pressure being provided by the flow generator is the awake pressure and the sleep state is determined to be asleep or sleep disordered breathing is detected.

3. The positive airway pressure device of claim 2, wherein the first pressure ramp rate is adjustable by a user.

4. The positive airway pressure device of claim 2, wherein the sensor is one of a flow sensor, a pressure sensor, a sound sensor, a motion sensor, or a plethysmograph.

5. The positive airway pressure device of claim 1, wherein the control system is further configured to control the flow generator to provide a pressure which decreases over time at a second pressure ramp rate when the pressure being provided by the flow generator is between the low pressure and the high pressure and the sleep state is determined to be awake.

6. The positive airway pressure device of claim 5, wherein the second pressure ramp rate is adjustable by a user.

7. The positive airway pressure device of claim 1, wherein the low pressure and the high pressure are adjustable by a user.

8. The positive airway pressure device of claim 1, wherein the control system is further configured to ignore sleep disordered breathing events when controlling the flow generator to transition from the awake pressure to a pressure between the low pressure and the high pressure.

9. The positive airway pressure device of claim 1, wherein the control system is further configured to control the flow generator to return from the awake pressure to a pressure between the low pressure and the high pressure in response to detection of sleep disordered breathing.

10. A positive airway pressure system, comprising:
the positive airway pressure device of claim 1;
a patient interface configured to provide to the patient the gas at the pressure; and
a conduit that provides a path for the gas from the flow generator to the patient interface.

11. A method of providing positive airway pressure therapy to a patient, the method comprising:
receiving input from a user to set an awake pressure;
detecting a presence of sleep disordered breathing;
determining a sleep state of the patient;
in response to the sleep state being determined to be asleep during a treatment session, delivering gas having an asleep pressure that is adjusted between a low asleep pressure that is greater than or equal to about 4 cmH2O and a high asleep pressure that is less than or equal to about 20 cmH2O, the asleep pressure depending at least in part on the presence of sleep disordered breathing; and
in response to the sleep state being determined to be awake based on breathing patterns detected from the patient after a previously determined asleep state during the treatment session, delivering gas having the awake pressure, the awake pressure lower than the low asleep pressure and being a therapeutic pressure greater than or equal to about 4 cmH2O.

12. The method of claim 11, further comprising increasing a pressure of the gas delivered at a first ramp rate when the pressure being delivered has the awake pressure and the sleep state is determined to be asleep or sleep disordered breathing is detected.

13. The method of claim 12, further comprising receiving input from a user to set the first ramp rate.

14. The method of claim 11, further comprising decreasing a pressure of the gas delivered at a second ramp rate when the pressure being delivered is between the low asleep pressure and the high asleep pressure and the sleep state is determined to be awake.

15. The method of claim 14, further comprising receiving input from a user to set the second ramp rate.

16. The method of claim 11, further comprising receiving input from a user to set the low asleep pressure and the high asleep pressure.

17. The method of claim 11, wherein detecting a presence of sleep disordered breathing comprises analyzing values from a sensor, the sensor comprising at least one of a flow sensor, a pressure sensor, a sound sensor, a motion sensor, or a plethysmograph.

18. A user interface communicably coupled to a control system of a positive airway pressure apparatus, the user interface comprising:
an awake pressure node configured to receive awake pressure data indicative of an awake pressure;
a low pressure node configured to receive lower bound data indicative of a lower bound of a pressure range; and
a high pressure node configured to receive upper bound data indicative of an upper bound of the pressure range,
wherein the lower bound of the pressure range is greater than or equal to about 4 cmH2O, and the upper bound of the pressure range is less than or equal to about 20 cmH2O,
wherein the user interface communicates the awake pressure, the lower bound of the pressure range, and the upper bound of the pressure range to the control system, and
wherein the control system controls the positive airway pressure apparatus to supply a breathing gas having the awake pressure in response to a sleep state being determined to be awake based on breathing patterns detected from the patient after a previously determined asleep state during a treatment session, the awake pressure being a therapeutic pressure greater than or equal to about 4 cmH2O, and the awake pressure less than the lower bound of the pressure range.

19. The user interface of claim 18, further comprising a ramp rate node configured to receive ramp rate data indicative of a pressure ramp rate.

20. The user interface of claim 19, wherein the control system transitions from providing the awake pressure to a pressure within the pressure range at the pressure ramp rate.

* * * * *